US012570616B2

(12) United States Patent
Wagner et al.

(10) Patent No.: US 12,570,616 B2
(45) Date of Patent: Mar. 10, 2026

(54) THERAPEUTIC COMPOUNDS

(71) Applicant: ARIZONA BOARD OF REGENTS ON BEHALF OF ARIZONA STATE UNIVERSITY, Scottsdale, AZ (US)

(72) Inventors: Carl E. Wagner, Glendale, AZ (US); Peter W. Jurutka, Scottsdale, AZ (US); Pamela A. Marshall, Glendale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 430 days.

(21) Appl. No.: 18/023,995

(22) PCT Filed: Sep. 8, 2021

(86) PCT No.: PCT/US2021/049461

§ 371 (c)(1),
(2) Date: Feb. 28, 2023

(87) PCT Pub. No.: WO2022/055995

PCT Pub. Date: Mar. 17, 2022

(65) Prior Publication Data

US 2023/0322688 A1 Oct. 12, 2023

Related U.S. Application Data

(60) Provisional application No. 63/076,839, filed on Sep. 10, 2020.

(51) Int. Cl.
*C07D 249/18* (2006.01)

(52) U.S. Cl.
CPC .................................. *C07D 249/18* (2013.01)

(58) Field of Classification Search
CPC .................................................... C07D 249/18
See application file for complete search history.

(56) References Cited

U.S. PATENT DOCUMENTS 4,938,949 A 7/1990 Borch et al.

FOREIGN PATENT DOCUMENTS

JP 2014076953 A 5/2014
WO 2010019391 A1 2/2010

OTHER PUBLICATIONS

Warda, Cells, 2023, vol. 12, 2575, 1of19-19of19. (Year: 2023).*
Jurthka, Int J Mol Sci, 2021, 22, 12371, 1-41. (Year: 2021).*
Zhylkibayev, Cells, 2025, vol. 1, 385, 1-18. (Year: 2025).*
Li, Int J Mol Med, vol. 4, 1963-1970, 2019. (Year: 2019).*
Syal, Ind J Clin Biochem 2015, 30(3), 323-328. (Year: 2015).*
Lerner, CNS Drugs, 2016, 30:269-280. (Year: 2016).*
Cesario , et al., "Differentiation and growth inhibition mediated via the RXR:PPARgamma heterodimer in colon cancer", Cancer Letters 240(2), 225-233 (2006).
Fantini, J , et al., "Bexarotene blocks calcium-permeable ion channels formed by neurotoxic Alzheimer's β-amyloid peptides.", ACS Chemical Neuroscience 5, 216-224 (2014).
Kakuta, H. , "Western-style Chinese (Kampo) medicine targeting retinoid X receptors (RXRs)", 248th ACS National Meeting, MEDI 102, San Francisco, CA. (Aug. 10-14, 2014).
Kawata, K, et al., "RXR partial agonist produced by side chain repositioning of alkoxy RXR full agonist retains antitype 2 diabetes activity without the adverse effects", J Med Chem 58(2), 912-926 (2015, epub 2014).
Kobayashi, T , et al., "Positron emission tomography to elucidate pharmacokinetic differences of regioisomeric retinoid x receptor agonists", ACS Med Chem Lett 6(3), 334-338 (2015).
Lerner , et al., "Bexarotene as add-on to antipsychotic treatment in schizophrenia patients: a pilot open-label trial.", Clinical Neuropharmacology 31(1), 25-33 (2008).
Liby , et al., "Synthetic Triterpenoids Prolong Survival in a Transgenic Mouse Model of Pancreatic Cancer", Cancer Prevention Research 3(11), 1427-1434 (2010).
Mcfarland, K, et al., "Low dose bexarotene treatment rescues dopamine neurons and restores behavioral function in models of Parkinson's disease", ACS Chemical Neuroscience 4, 1430-1438 (2013).
Mortelmans, Z , "The Amse *Salmonella*/microsome mutagenicity assay", Mutat Res 455, 29-60 (2000).
Mukherjee , et al., "Sensitization of diabetic and obese mice to insulin by retinoid X receptor agonists", Nature 386, 407-410 (1997).
Patent Cooperation Treaty , International Search Report and Written Opinion for PCT/US2021/049461, 6 pages, dated Dec. 22, 2021.
Pubchem, CID 115541637, 7 pages (Jan. 29, 2016).
Pubchem , CID 115931957, 7 pages (Jan. 30, 2016).
Pubchem , CID 82769697, 8 pages (Oct. 20, 2014).
Takamatsu, K, et al., "The First Potent Subtype-Selective Retinoid X Receptor (RXR) Agonist Possessing a 3-Isopropoxy-4-isopropylphenylamino Moiety, NEt-3IP (RXRalpha/beta-dual agonist).", ChemMedChem 3, 780-787 (2008).
Yen, W, et al., "A selective retinoid X receptor agonist bexarotene (Targretin) prevents and overcomes acquired paclitaxel (Taxol) resistance in human non-small cell lung cancer", Clinical Cancer Research 10(24), 8656-8664 (2004).

* cited by examiner

*Primary Examiner* — D Margaret M Seaman
(74) *Attorney, Agent, or Firm* — Viksnins Harris Padys Malen LLP

(57) ABSTRACT

The invention provides compounds formula (I) and salts thereof: wherein $R^1$-$R^2$ have any of the values defined in the specification. The compounds are useful for treating conditions including Alzheimer's disease, Parkinson's disease, diabetes, cancer, inflammation, hyperresponsiveness, allergic conditions, asthma, and psychotic disorders such as schizophrenia. The compounds are also useful to lower IL-4, IL-5, or IL-15 levels in an animal.

(I)

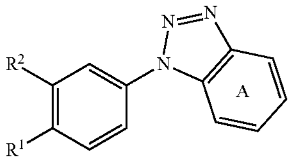

15 Claims, No Drawings

THERAPEUTIC COMPOUNDS

CROSS-REFERENCE TO RELATED APPLICATION

This application claims priority to U.S. Provisional Application No. 63/076,839 that was filed on Sep. 10, 2020. The entire content of the application referenced above is hereby incorporated by reference herein.

BACKGROUND

The human retinoid X receptors (hRXRs) consist of three identified isoforms (α, β, γ) that function as transcription promoters often in partnership with other members of a larger nuclear receptor (NR) family of transcription regulators including the thyroid receptor (TR), the vitamin D receptor (VDR), the liver X receptor (LXR), the peroxisome proliferator-activated receptor (PPAR), and the retinoic acid receptor (RAR). While 9-cis-retinoic acid (9-cis-RA) and docosahexaenoic acid (DHA) have been shown to bind to hRXRs and promote RXR element (RXRE) regulated transcription (i.e. function as RXR agonists), it is still unclear if RXR has a bona fide endogenous molecular ligand. RXR has been described as the central NR regulator, because it often plays a critical role, either as a permissive or non-permissive partner, in heterodimer complexes that must be formed with the other NRs to regulate their respective response elements.

Recent studies have identified several RXR-selective-binding molecular ligands (rexinoids) that can modulate not only RXRE regulated transcription but also the heterodimer regulated transcription of other NRs. For instance, RXR is a subordinate partner in the RXR-RAR heterodimer, otherwise referred to as a non-permissive heterodimer, since transcription is not promoted in the RAR unliganded (apo-RAR) heterodimer with RXR. Additionally, the RXR-TR heterodimer is non-permissive. In contrast to these non-permissive heterodimers, permissive heterodimers such as RXR-PPAR allow transcription to be promoted in the presence of either RXR or PPAR agonists. The RXR-LXR heterodimer is also permissive. Hence, there is enormous potential for RXR agonists to activate or repress various biological pathways and effect therapeutic results for various conditions that would benefit from activation or repression of a specific pathway.

Bexarotene has been used to treat cutaneous T cell lymphoma. Bexarotene has also been shown to be useful for treatment of Alzheimer's Disease (AD). However, bexarotene treatment results in untoward side effects, possibly due to its nonspecific nature of binding RXR in several states, including the RXR-RXR homodimer form as well as RXR heterodimer forms.

McFarland, K., et al, *ACS Chem. Neurosci.,* 2013, 4(11), 1430-1438 treated a rat model of Parkinson's disease (PD) with bexarotene and noted marked improvement in the PD symptoms. Specifically the bexarotene restored dopamine cells and natural behavior in the PD model. As importantly, the bexarotene dose that accomplished this was quite low, alleviating some side effects. The researchers demonstrated that these symptoms were alleviated by bexarotene binding to RXR and its heterodimerizing with another nuclear recpetor called Nurr1.

PD is a chronic, debilitating disorder in which the neurons of the central nervous system degenerate over time. Specifically the dopamine secreting cells of the midbrain slowy die off, leaving the patient with a wide range of symptoms due to the lack of dopamine. Early symptoms include shaking, off balance gait, and slowless of muscles. Over time, symptoms worsen and additional symptoms including demetia and/or depression can develop. Treatments include dopamine agonists, given to try to ameliorate the effect of loss of dopamine in the system.

The compounds Net-41B and 100 have been reported to be effective as a retinoid-X-receptor (RXR) agonist with reduced side effect profiles. Kakuta, H. "Western-style Chinese (Kampo) medicine targeting retinoic X receptors (RXRs)." 248$^{th}$ ACS National Meeting; San Francisco, CA 2014; and Kakuta, H. "Retinoid X receptor partial agonist and pharmaceutical agent containing the same" from Jpn. Kokai Tokkyo Koho (2014), JP 2014076953 A 20140501.

NEt-41B

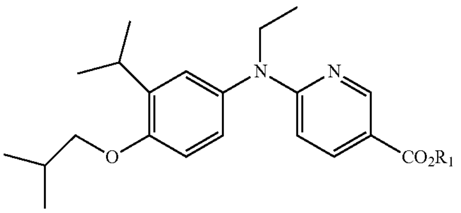

100

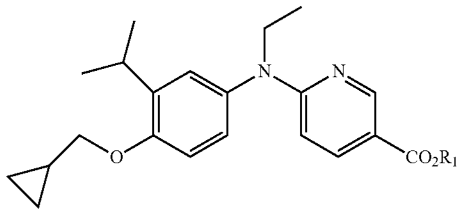

Additionally compound 101-104 have been reported to be effective as retinoid-X-receptor (RXR) agonists with potential as a therapeutic agent for treating for human cancers (Takamatsu, K., et al., *ChemMedChem* 2008, 3, 780-787).

101

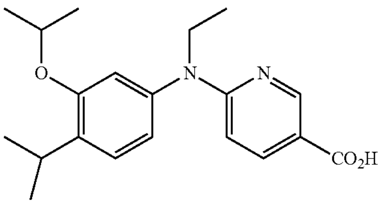

102

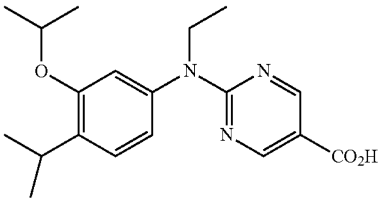

103

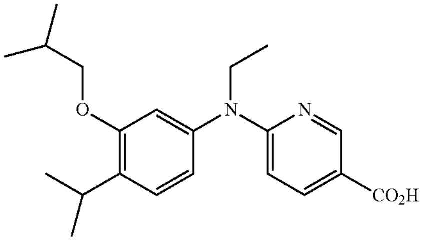

-continued

104

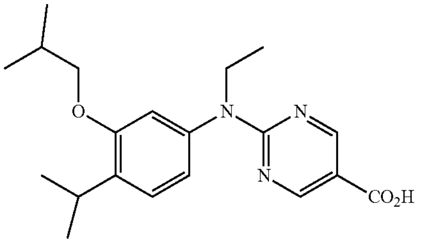

105

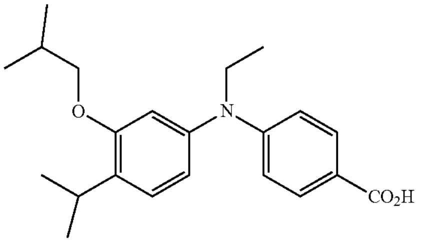

Compound 105 has also been reported.

Currently there is a need for additional chemical agents that are useful for treating conditions including Alzheimer's disease, Parkinson's disease, diabetes, cancer, and psychotic disorders such as schizophrenia.

SUMMARY

The present invention provides compounds that are useful for treating conditions including Alzheimer's disease, Parkinson's disease, diabetes, cancer, and psychotic disorders such as schizophrenia.

Accordingly, in a first embodiment (Embodiment 1; abbreviated as "E1") the invention provides a compound of the invention, which is a compound of Formula (I), or a salt thereof:

(I)

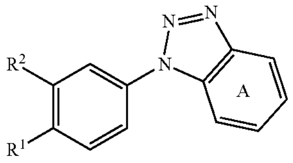

wherein:

- $R^1$ is $(C_3-C_6)$alkyl, $(C_3-C_6)$cycloalkyl-$(C_1-C_3)$alkyl-, $(C_3-C_6)$alkoxy, or $(C_3-C_6)$cycloalkyl-$(C_1-C_3)$alkoxy-;
- $R^2$ is $(C_3-C_6)$alkyl, $(C_3-C_6)$cycloalkyl-$(C_1-C_3)$alkyl-, $C_3-C_6)$alkoxy, or $(C_3-C_6)$cycloalkyl-$(C_1-C_3)$alkoxy-;
- Ring A is substituted with a group —$CO_2R^c$ and is optionally further substituted on a carbon atom with one or more groups independently selected from halo, hydroxy, nitro, cyano, —$NR^aR^b$, $(C_1-C_6)$alkyl, $(C_2-C_6)$alkenyl, $(C_2-C_6)$alkynyl, $(C_3-C_6)$cycloalkyl, $(C_1-C_6)$alkoxy, $(C_1-C_6)$alkoxycarbonyl, and $(C_1-C_6)$alkanoyloxy, wherein each $(C_1-C_6)$alkyl, $(C_2-C_6)$alkenyl, $(C_2-C_6)$alkynyl, $(C_3-C_6)$cycloalkyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, —$NR^aR^b$, and oxo (=O);
- $R^a$ and $R^b$ are each independently H or $(C_1-C_6)$alkyl; or $R^a$ and $R^b$ taken together with the nitrogen to which they are attached form a ring selected from aziridine, azetidino, pyrrolidino, and morpholino; and
- $R^c$ is H or $(C_1-C_6)$alkyl.

Further embodiments (E2-E13) are described below.

In another embodiment E2, the invention provides a compound or salt of E1, which is a compound of formula (Ia):

(Ia)

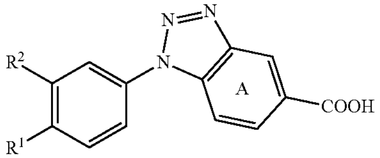

or a salt thereof, wherein:

Ring A is optionally substituted on a carbon atom with one or more groups independently selected from halo, hydroxy, nitro, cyano, —$NR^aR^b$, $(C_1-C_6)$alkyl, $(C_2-C_6)$alkenyl, $(C_2-C_6)$alkynyl, $(C_3-C_6)$cycloalkyl, $(C_1-C_6)$alkoxy, $(C_1-C_6)$alkoxycarbonyl, and $(C_1-C_6)$alkanoyloxy, wherein each $(C_1-C_6)$alkyl, $(C_2-C_6)$alkenyl, $(C_2-C_6)$alkynyl, $(C_3-C_6)$cycloalkyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, —$NR^aR^b$, and oxo (=O).

In another embodiment E3, the invention provides a compound or salt of E1 or E2, wherein $R^1$ is $(C_3-C_6)$alkyl or $(C_3-C_6)$cycloalkyl-$(C_1-C_3)$alkyl-.

In another embodiment E4, the invention provides a compound or salt of E1 or E2, wherein $R^1$ is isopropyl or cyclopropylmethyl.

In another embodiment E5, the invention provides a compound or salt of E1 or E2, wherein $R^1$ is $(C_3-C_6)$alkoxy, or $(C_3-C_6)$cycloalkyl-$(C_1-C_3)$alkoxy-.

In another embodiment E6, the invention provides a compound or salt of E1 or E2, wherein $R^1$ is 2-methylpropoxy.

In another embodiment E7, the invention provides a compound or salt of E1, E2, E3, E4, E5, or E6, wherein $R^2$ is $(C_3-C_6)$alkyl or $(C_3-C_6)$cycloalkyl-$(C_1-C_3)$alkyl-.

In another embodiment E8, the invention provides a compound or salt of E1, E2, E3, E4, E5, or E6, wherein $R^2$ is isopropyl.

In another embodiment E9, the invention provides a compound or salt of E1, E2, E3, E4, E5, or E6, wherein $R^2$ is $(C_3-C_6)$alkoxy, or $(C_3-C_6)$cycloalkyl-$(C_1-C_3)$alkoxy-.

In another embodiment E10, the invention provides a compound or salt of E1, E2, E3, E4, E5, or E6, wherein $R^2$ is 2-methylpropoxy, isopropoxy, or cyclopropylmethoxy.

In another embodiment E11, the invention provides a compound or salt of E1, E2, E3, E4, E5, or E6, wherein $R^2$ is isopropyl, isopropoxy, or 2-methylpropoxy.

In another embodiment E12, the invention provides a compound or salt of E1, wherein $R^1$ is isopropyl, cyclopropylmethyl, or 2-methylpropoxy; and $R^2$ is isopropyl, isopropoxy, or 2-methylpropoxy.

In another embodiment E13, the invention provides a compound or salt selected from the group consisting of:

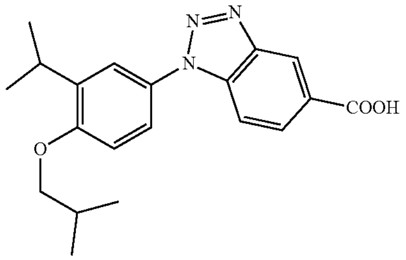 [SMILES: CC(C)COc1ccc(-n2nnc3cc(C(=O)O)ccc32)cc1C(C)C]

and salts thereof.

The invention also provides a pharmaceutical composition comprising a compound of formula (I), or a pharmaceutically acceptable salt thereof, and a pharmaceutically acceptable diluent or carrier.

The invention also provides a method for treating Alzheimer's disease, Parkinson's disease, diabetes, cancer, or a psychotic disorder in an animal (e.g. a mammal such as a human) comprising administering to the animal a compound of formula (I), or a pharmaceutically acceptable salt thereof.

The invention also provides a compound of formula (I), or a pharmaceutically acceptable salt thereof, for the prophylactic or therapeutic treatment of Alzheimer's disease, Parkinson's disease, diabetes, cancer, or a psychotic disorder.

The invention also provides the use of a compound of formula (I), or a pharmaceutically acceptable salt thereof, to prepare a medicament useful for treating Alzheimer's disease, Parkinson's disease, diabetes, cancer, or a psychotic disorder in an animal.

The invention also provides a method for activating RXR in a cell comprising contacting the cell in vitro or in vivo with an effective amount of a compound of formula (I), or a salt thereof.

The invention also provides a compound of formula (I), or a pharmaceutically acceptable salt thereof, for use in medical therapy.

The invention also provides a method to reduce inflammation or hyperresponsiveness in an animal comprising administering a compound of formula (I) or a pharmaceutically acceptable salt thereof, to the animal.

The invention also provides a method to lower IL-4, IL-5, or IL-15 levels in an animal comprising administering a compound of formula (I) or a pharmaceutically acceptable salt thereof, to the animal.

The invention also provides a method to treat an allergic condition in an animal comprising administering a compound of formula (I) or a pharmaceutically acceptable salt thereof, to the animal.

The invention also provides a method to treat asthma in an animal comprising administering a compound of formula (I) or a pharmaceutically acceptable salt thereof, to the animal.

The invention also provides a compound of formula (I) or a pharmaceutically acceptable salt thereof, for the prophylactic or therapeutic treatment of inflammation or hyperresponsiveness.

The invention also provides a compound of formula (I) or a pharmaceutically acceptable salt thereof, to lower IL-4, IL-5, or IL-15 levels in an animal.

The invention also provides a compound of formula (I) or a pharmaceutically acceptable salt thereof, for the prophylactic or therapeutic treatment of an allergic condition.

The invention also provides a compound of formula (I) or a pharmaceutically acceptable salt thereof, for the prophylactic or therapeutic treatment of asthma.

The invention also provides the use of a compound of formula (I) or a pharmaceutically acceptable salt thereof, to prepare a medicament useful to reduce inflammation or hyperresponsiveness in an animal.

The invention also provides the use of a compound of formula (I) or a pharmaceutically acceptable salt thereof, to prepare a medicament useful to lower IL-4, IL-5, or IL-15 levels in an animal.

The invention also provides the use of a compound of formula (I) or a pharmaceutically acceptable salt thereof, to prepare a medicament useful to treat an allergic condition in an.

The invention also provides the use of a compound of formula (I) or a pharmaceutically acceptable salt thereof, to prepare a medicament useful to treat asthma in an animal.

The invention also provides a method to treat diabetes (e.g. Type II diabetes) in an animal comprising administering a compound of formula (I) or a pharmaceutically acceptable salt thereof, to the animal.

The invention also provides a compound of formula (I) or a pharmaceutically acceptable salt thereof, for the prophylactic or therapeutic treatment of diabetes (e.g. Type II diabetes).

The invention also provides the use of a compound of formula (I) or a pharmaceutically acceptable salt thereof, to prepare a medicament useful to treat diabetes (e.g. Type II diabetes) in an animal (e.g. a human).

The invention also provides processes and novel intermediates that are useful for preparing a compound of formula (I), or a salt thereof.

In one embodiment, the invention provides compounds that are partial RXR agonists. These compounds may incite fewer or less severe RXR agonist side effects.

DETAILED DESCRIPTION

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. The term "activating", such as used in the phrase "activating RXR", means to promote transcriptional activity.

The term "treatment" or "treating," to the extent it relates to a disease or condition includes preventing the disease or condition from occurring, inhibiting the disease or condition, eliminating the disease or condition, and/or relieving one or more symptoms of the disease or condition.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents.

Specifically, $(C_1\text{-}C_6)$alkyl can be methyl, ethyl, propyl, isopropyl, butyl, iso-butyl, sec-butyl, pentyl, 3-pentyl, or hexyl; $(C_3\text{-}C_6)$cycloalkyl can be cyclopropyl, cyclobutyl, cyclopentyl, or cyclohexyl; $(C_3\text{-}C_6)$cycloalkyl$(C_1\text{-}C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1\text{-}C_6)$alkoxy can be methoxy, ethoxy, propoxy, isopropoxy, butoxy, iso-butoxy, sec-butoxy, pentoxy, 3-pentoxy, or hexyloxy; $(C_2\text{-}C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2\text{-}C_6)$ alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1\text{-}C_6)$alkanoyl can be acetyl, propanoyl or butanoyl; $(C_1\text{-}C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1\text{-}C_6)$alkanoyloxy can be formyloxy, acetoxy, propanoyloxy, butanoyloxy, isobutanoyloxy, pentanoyloxy, or hexanoyloxy; aryl can be phenyl, indenyl, or naphthyl; and heteroaryl can be pyrazinyl, pyridazine, triazine, pyridyl, or pyrimidinyl, or an N-oxide thereof.

Diseases and Condition

Compounds of the invention possessing RXR agonist properties are useful for treating Alzheimer's disease. The compounds of the invention may also treat Alzheimer's disease by targeting a combination of RXR:LXR controlled genes (like ApoE), or by binding to amyloid beta oligomers (where cholesterol usually binds) and disrupting calcium channel formation in neurons (Fantini, J. et al. *ACS Chem. Neurosci.* 2014, DOI: 10.1021/cn400183w).

Compounds of the invention are also useful for treating cancers, including but not limited to, colon, breast, lung, pancreatic, skin, cutaneous T-cell lymphoma, acute promyelocytic leukemia, ovarian, bladder, kidney, head and neck cancers, and Kaposi's sarcoma. See breast cancer: Esteva, F. J. et al. *JCO,* 2003, 21, 999-1006; advanced non-small lung cancer: (a) Khuri, F. R. et al. *JCO,* 2001, 19, 2626-2637 and (b) Lamph, W. W. et al. *Clin. Cancer Res.* 2004, 10, 8656-8664; pancreatic cancer: Liby, K. *Cancer Prev. Res.* 2010, 3, 1427-1434; and colon cancer: Cesario, R. M. et al. *Cancer Letters* 2006, 240, 225-233.

Compounds of the invention possessing RXR agonist properties and/or that target the Nurr1 receptor are useful for treating Parkinson's disease (see McFarland, K., et al, *ACS Chem. Neurosci.,* 2013, 4(11), 1430-1438), while compounds of the invention possessing RXR agonist properties and/or PPARg activity may be useful for treating diabetes (see Mukherjee, R. et al. *Nature,* 1997, 386, 407-410).

The compounds of the invention may also be useful for treating, psychotic disorders such as schizophrenia. Such treatment may also be carried out in combination with other antipsychotic treatments (see Lerner, V. et al. *Clin. Neuropharmacol.* 2008, 31, 25-33).

In cases where compounds are sufficiently basic or acidic, a salt of a compound of the invention can be useful as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949. Compounds that are non-toxic and non-mutagenic at typical dose levels will have useful doses. (Mortelmans, K.; Zeiger, E. "The Ames *Salmonella*/microsome mutagenicity assay." Mutat. Res. 2000, 455, 29-60).

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds can also be administered in combination with other therapeutic agents. In certain embodiments, compounds of the invention can be administered in combination with agents that are useful for the treatment of diseases associated with dopamine deficiency. For example, the compounds can be administered (and/or formulated) with clozapine, olanzapine, haloperidol, risperidone, perphenazine, quetiapine, or chlorpromazine.

The ability of a compound of the invention to act as an RXR agonist (e.g. to promote or activate RXR, i.e., promote or activate RXR regulated gene expression) may be determined using pharmacological models which are well known to the art, or using Test A or Test B described below.

Test A. RXR Selective Agonist Assay (Mammalian Two-Hybrid Assay).

Compounds are tested for RXR selective agonist activity via a mammalian two-hybrid assay in human colon cancer cells, HCT-116. The cell line is transfected with pCMVhRXR binding domain vector (BD), hRXR activation domain (AD), pFR-Luc reporter gene containing BD-binding sites, and a *renilla* control plasmid. Cells are transfected for 18 hours utilizing a liposome-mediated transfection protocol then exposed to either the ethanol vehicle or $10^{-7}$ M Bexarotene or the indicted analog. After 24 hours the cells are lysed and a luciferase assay was completed. Analog dependent RXR binding and homodimerization, as measured by luciferase output, is compared to the parent compound Bexarotene.

Test B. RXR Agonist Assay (RXRE-Luciferase Based Assay).

An RXRE-luciferase assay is run at 25 nM in HCT-116 cells. The RXRE assays are completed using HCT-116 cells plated at 100,000 cells/well in 24 well plates. The cells are co-transfected using 250 ng of a RXRE-luciferase reporter plasmid (RXRE from the naturally occurring responsive element in the rat cellular retinol binding protein II gene), 50 ng of pSG5-human RXRα vector, 20 ng of the *renilla* control plasmid and 2 μL/well of Polyjet transfection reagent for liposome-mediated delivery of the DNA. The cells are treated with ethanol or analogs (final concentration of 25 nM) for 24-hours post-transfection. After a 24-hour incubation period, the amount of rexinoid activity is measured using luciferase output via a dual-luciferase reporter assay system according to the manufacturer's protocol (Promega, Madison, WI) in a Sirus luminometer (Berthold Detection System, Pforzheim, Germany). Two independent assays are conducted with four samples for each treatment group.

The invention will now be illustrated by the following non-limiting Examples.

EXAMPLES

Example 1 Synthesis of Compound 54

Aniline 37 was coupled to methyl 4-iodo-3-nitrobenzoate (46) with tris(dibenzylidene-acetone)-dipalladium in the presence of rac-BINAP and cesium carbonate to give methyl 4-((4-isobutoxy-3-isopropylphenyl)amino)-3-nitrobenzoate (47) in 54% yield (Scheme 1).

Scheme 1

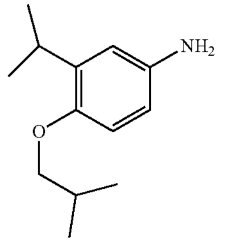

37

+

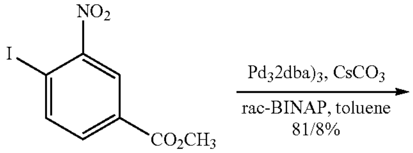

46

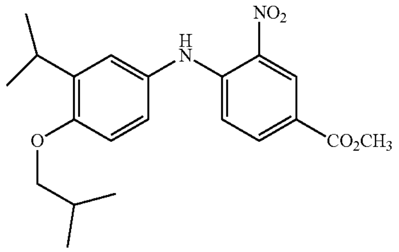

47

Compound 47, was reduced with Pd/C to give 52 in quantitative yield. Compound 52 was treated with sodium nitrite and sulfuric acid in THF to give methyl 1-(4-isobutoxy-3-isopropylphenyl)-1H-benzo[d][1,2,3]triazole-5-carboxylate (53) in 87.6% yield (Scheme 2).

Scheme 2

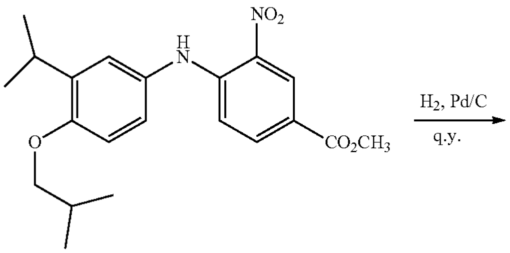

47

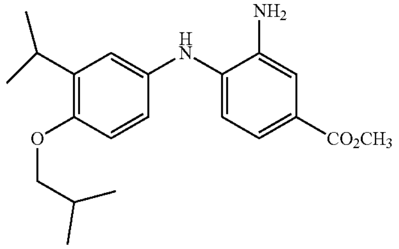

52

-continued

52

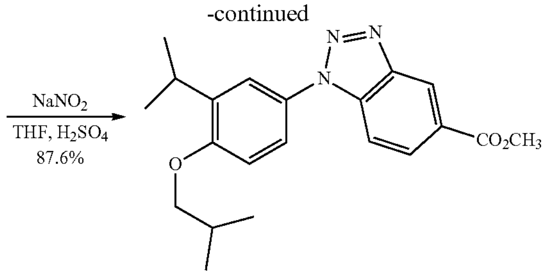

53

Methyl ester 53 was also saponified in methanolic potassium hydroxide followed by acidification with hydrochloric acid to give 1-(4-isobutoxy-3-isopropylphenyl)-1H-benzo[d][1,2,3]triazole-5-carboxylic acid (54) in 71.4% (Scheme 3).

Scheme 3

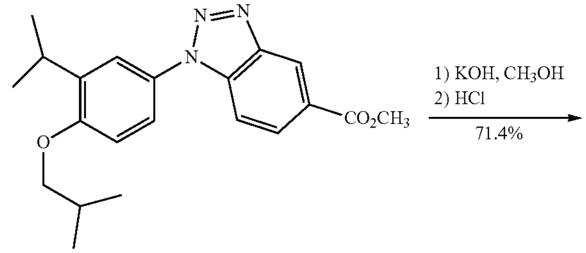

53

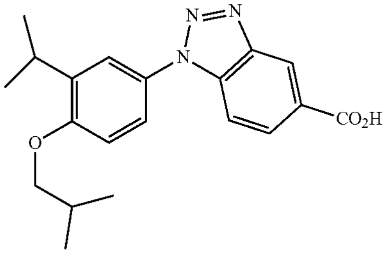

54 a. Preparation of Methyl 4-((4-isobutoxy-3-isopropylphenyl)amino)-3-nitrobenzoate (47)

To a solution of compound 37 (1.68 g, 8.10 mmol), methy 4-iodo-3-nitrobenzoate 46 (2.63 g, 8.57 mmols), $CsCO_3$ (5.44 g, 16.7 mmol), rac-BINAP (0.4286 g, 0.7472 mmol) in toluene (10.8 mL) in a 100 mL round-bottomed flask was added $Pd_2(dba)_3$ (0.404 g, 2.31 mmol). The solution was sparged with nitrogen for 5 min., then a reflux condenser was fitted to the flask, the atmosphere was evacuated and back-filled with nitrogen (three times), and the reaction was heated to reflux with stirring in an oil bath (125-120° C.) for 22 h. After cooling the reaction to room temperature, excess cesium carbonate and other solid particulates were filtered and washed with ethyl acetate, and the organic filtrate was concentrated in vacuo to give a crude product that was purified by column chromatography (150 mL $SiO_2$, 4% ethyl acetate: hexanes to 12% ethyl acetate: hexanes) to give 47 (2.5619 g, 81.8%) as a crystalline solid, m.p. 78.1-82.3° C.: $^1$H NMR (400 MHZ, $CDCl_3$) δ 9.71 (br s, 1H), 8.90 (d, J=2.0, 1H), 7.90 (ddd, J=9.2, 2.0, 0.4, 1H), 7.07 (d, J=2.8, 1H), 7.04 (dd, J=8.8, 2.8, 4H), 7.00 (d, J=8.8, 1H), 6.86 (d, J=8.4, 1H), 3.89 (s, 3H), 3.77 (d, J=6.4, 2H), 3.37 (hept, J=6.8, 1H), 2.13 (nonet, J=6.8, 1H), 1.22 (d, J=6.8, 6H), 1.07 (d, J=6.8, 6H); $^{13}$C NMR (100.6 MHz, $CDCl_3$) δ 165.4, 155.2, 147.2, 138.9, 135.7, 131.5, 129.5, 129.2, 128.9, 128.3, 124.0, 123.9, 118.2, 115.5, 111.7, 74.5, 52.0, 28.4, 26.9, 22.4, 19.3; IR (neat) 3340, 2958, 1716, 1705, 1622, 1212, 757 $cm^{-1}$; ES-MS (M+Na)+ calcd for $C_{21}H_{26}N_2O_5Na$ 409.1740, found 409.1750.

b. Preparation of Methyl 3-amino-4-((4-isobutoxy-3-isopropylphenyl)-amino)benzoate (52)

A solution of compound 47 (1.2000 g, 3.105 mmols) in ethyl acetate (63 mL) was passed through a 10% Pd/C cartridge at 1.0 mL/minute in the ThalesNano H-cube® at 65° C. and 2-5 bar pressure. The resulting solution was concentrated in vacuo to give 52 (quantitative yield) as a yellow oil that was used without further purification: $^1$H NMR (400 MHZ, $CDCl_3$) δ 7.47 (d, J=2.0, 1H), 7.45 (dd, J=5.6, 2.0, 1H), 6.95 (d, J=8.8, 1H), 6.94 (d, J=2.8, 1H), 6.83 (dd, J=8.8, 2.8, 1H), 6.78 (d, J=8.8, 1H), 5.52 (br s, 1H), 3.85 (s, 3H), 3.72 (d, J=6.4), 3.50 (br s, 2H), 3.35 (hept, J=6.8, 1H), 2.13 (nonet, J=6.8, 1H), 1.20 (d, J=6.8, 6H), 1.06 (d, J=6.8, 6H); $^{13}$C NMR (100.6 MHz, $CDCl_3$) δ 167.2, 152.4, 139.3, 138.3, 134.7, 134.2, 122.9, 121.6, 119.6, 118.8, 114.1, 111.9, 60.3, 51.6, 28.5, 26.9, 22.5, 21.0, 19.4, 14.1; IR (neat) 3379, 2959, 1697, 1496, 1296 cm-1; ES-MS (M+Na)+ calcd for $C_{21}H_{28}N_2O_3Na$ 379.1998, found 379.1998.

c. Preparation of Methyl 1-(4-isobutoxy-3-isopropylphenyl)-1H-benzo[d][1,2,3]triazole-5-carboxylate (53)

To a solution of compound 52 (1.0839 g, 3.04 mmols) in THF (14.0 mL) at 0° C. was added a 1:1 solution of concentrated sulfuric acid and water (14.0 mL) followed by a solution of $NaNO_2$ (0.3292 g, 4.77 mmols) in water (14.0 mL), and the reaction was allowed to warm to room temperature and stirred for 1 hour. The reaction was poured into ethyl acetate, extracted, and the organic layers were combined, washed with saturated sodium bicarbonate and brine, dried over sodium sulfate, filtered, and concentrated to give crude 53 which was purified by column chromatography (150 mL $SiO_2$, 4%-6% ethyl acetate:hexanes) to give 53 (0.9791 g, 87.6%) as a crystalline solid, m.p. 86-89° C.: $^1$H NMR (400 MHZ, $CDCl_3$) δ 8.83 (d, J=0.8, 1H), 8.19 (dd, J=8.8, 1.6, 1H), 7.65 (dd, J=8.8, 0.4, 1H), 7.53 (d, J=2.8, 1H), 7.45 (dd, J=8.8, 2.8, 1H), 6.99 (d, J=8.8, 1H), 3.98 (s, 3H), 3.82 (d, J=6.0, 2H), 3.44 (hept, J=6.8, 1H), 2.18 (nonet, J=6.4, 1H), 1.28 (d, J=6.8, 6H), 1.09 (d, J=6.4, 6H); $^{13}$C NMR (100.6 MHZ, $CDCl_3$) δ 166.4, 156.8, 145.9, 138.9, 134.8, 129.0, 128.6, 126.4, 122.9, 121.5, 121.4, 111.4, 110.2, 52.4, 28.4, 27.1, 22.3, 19.3; IR (neat) 2962, 1711, 1616, 1505, 1471, 1239, 750 cm-1; ES-MS (M+Na)+ calcd for $C_{21}H_{25}N_3O_3Na$ 390.1794, found 390.1794.

d. Preparation of 1-(4-Isobutoxy-3-isopropylphenyl)-1/I-benzo[d][1,2,3]triazole-5-carboxylic acid (54)

To a solution of compound 53 (0.7544 g, 2.053 mmols) in methanol (5.2 mL) was added a solution of KOH (0.3795 g, 6.764 mmols) in water (0.45 mL) and the solution was heated to reflux with stirring for 1 hour. The solution was then cooled to room temperature, quenched with 1N HCl (80 mL), and the resulting precipitate was filtered to give a crude product that was purified by column chromatography (150 mL $SiO_2$, 20%-60% ethyl acetate:hexanes) to give 54 (0.5182 g, 71.4%) as a crystalline solid, m.p. 177.3-178.7° C.: $^1$H NMR (400 MHZ, $CDCl_3$) δ10.91 (br s, 1H), 8.98 (t, J=0.8, 1H), 8.27 (dd, J=8.8, 1.6, 1H), 7.71 (dd, J=8.8, 0.4, 1H), 7.55 (d, J=2.4, 1H), 7.47 (dd, J=8.8, 2.4, 1H), 7.01 (d, J=8.8, 1H), 3.84 (d, J=6.4, 2H), 3.45 (hept, J=6.8, 1H), 2.19 (nonet, J=6.8, 1H), 1.30 (d, J=6.8, 6H), 1.10 (d, J=6.8, 6H); $^{13}$C NMR (100.6 MHz, $CDCl_3$) δ 171.3, 156.9, 145.8, 139.0, 135.3, 129.0, 128.9, 125.7, 124.0, 121.6, 121.5, 111.5, 110.4, 74.7, 28.4, 27.1, 22.4, 19.3; IR (neat) 2955, 1675, 1613, 1495, 1302, 1242, 1028, 814 cm-1; ES-MS (M-H)-calcd for $C_{20}H_{22}N_3O_3$ 352.1661, found 352.1657. Anal. Calcd for $C_{20}H_{23}N_3O_3$: C, 67.97; H, 6.56; N, 11.89. Found: C, 68.06; H, 6.58; N, 11.92.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I), or a salt thereof:

(I)

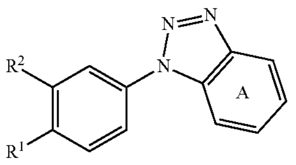

wherein:

$R^1$ is ($C_3$-$C_6$)alkyl, ($C_3$-$C_6$)cycloalkyl-($C_1$-$C_3$)alkyl-, ($C_3$-$C_6$)alkoxy, or ($C_3$-$C_6$)cycloalkyl-($C_1$-$C_3$)alkoxy-;

$R^2$ is ($C_3$-$C_6$)alkyl, ($C_3$-$C_6$)cycloalkyl-($C_1$-$C_3$)alkyl-, $C_3$-$C_6$)alkoxy, or ($C_3$-$C_6$)cycloalkyl-($C_1$-$C_3$)alkoxy-;

Ring A is substituted with a group —$CO_2R^c$ and is optionally further substituted on a carbon atom with one or more groups independently selected from halo, hydroxy, nitro, cyano, —$NR^aR^b$, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkoxycarbonyl, and ($C_1$-$C_6$) alkanoyloxy, wherein each ($C_1$-$C_6$)alkyl, ($C_2$-$C_6$) alkenyl, ($C_2$-$C_6$)alkynyl, ($C_3$-$C_6$)cycloalkyl, ($C_1$-$C_6$) alkoxy, ($C_1$-$C_6$)alkoxycarbonyl, and ($C_1$-$C_6$) alkanoyloxy, is optionally substituted with one or more groups independently selected from halo, hydroxy, nitro, cyano, ($C_1$-$C_6$)alkoxy, —$NR^aR^b$, and oxo (═O);

$R^a$ and $R^b$ are each independently H or ($C_1$-$C_6$)alkyl; or $R^a$ and $R^b$ taken together with the nitrogen to which they are attached form a ring selected from aziridine, azetidino, pyrrolidino, and morpholino; and $R^c$ is H or ($C_1$-$C_6$)alkyl.

2. The compound or salt of claim 1, which is a compound of formula (Ia):

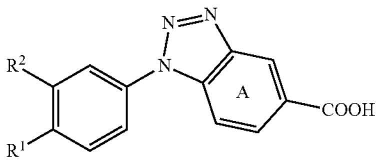

(Ia)

or a salt thereof, wherein:

Ring A is optionally substituted on a carbon atom with one or more groups independently selected from halo, hydroxy, nitro, cyano, —$NR^aR^b$, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkoxycarbonyl, and ($C_1$-$C_6$) alkanoyloxy, wherein each ($C_1$-$C_6$)alkyl, ($C_2$-$C_6$) alkenyl, ($C_2$-$C_6$)alkynyl, ($C_3$-$C_6$)cycloalkyl, ($C_1$-$C_6$) alkoxy, ($C_1$-$C_6$)alkoxycarbonyl, and ($C_1$-$C_6$) alkanoyloxy, is optionally substituted with one or more groups independently selected from halo, hydroxy, nitro, cyano, ($C_1$-$C_6$)alkoxy, —$NR^aR^b$, and oxo (═O).

3. The compound or salt of claim 1, wherein $R^1$ is ($C_3$-$C_6$)alkyl or ($C_3$-$C_6$)cycloalkyl-($C_1$-$C_3$)alkyl-.

4. The compound or salt of claim 1, wherein $R^1$ is isopropyl or cyclopropylmethyl.

5. The compound or salt of claim 1, wherein $R^1$ is ($C_3$-$C_6$)alkoxy, or ($C_3$-$C_6$)cycloalkyl-($C_1$-$C_3$)alkoxy-.

6. The compound or salt of claim 1, wherein $R^1$ is 2-methylpropoxy.

7. The compound or salt of claim 1, wherein $R^2$ is ($C_3$-$C_6$)alkyl or ($C_3$-$C_6$)cycloalkyl-($C_1$-$C_3$)alkyl-.

8. The compound or salt of claim 1, wherein $R^2$ is isopropyl.

9. The compound or salt of claim 1, wherein $R^2$ is ($C_3$-$C_6$)alkoxy, or ($C_3$-$C_6$)cycloalkyl-($C_1$-$C_3$)alkoxy-.

10. The compound or salt of claim 1, wherein $R^2$ is 2-methylpropoxy, isopropoxy, or cyclopropylmethoxy.

11. The compound or salt of claim 1, wherein $R^2$ is isopropyl, isopropoxy, or 2-methylpropoxy.

12. The compound or salt of claim 1, wherein $R^1$ is isopropyl, cyclopropylmethyl, or 2-methylpropoxy; and $R^2$ is isopropyl, isopropoxy, or 2-methylpropoxy.

13. The compound or salt of claim 1 selected from the group consisting of:

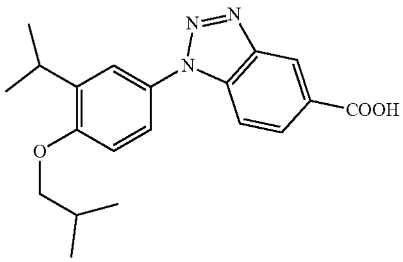 [SMILES: CC(C)COc1ccc(-n2nnc3cc(C(=O)O)ccc32)cc1C(C)C]

and salts thereof.

14. A pharmaceutical composition comprising a compound as described in claim 1 or a pharmaceutically acceptable salt thereof, and a pharmaceutically acceptable carrier.

15. A method for treating cancer in an animal comprising administering a compound as described in claim 1 or a pharmaceutically acceptable salt thereof, to the animal.

* * * * *